US008717564B2

(12) United States Patent
Bishop

(10) Patent No.: US 8,717,564 B2
(45) Date of Patent: May 6, 2014

(54) OPTICAL SEDIMENTATION RECORDER

(75) Inventor: James K. B. Bishop, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 346 days.

(21) Appl. No.: 12/742,395

(22) PCT Filed: Nov. 7, 2008

(86) PCT No.: PCT/US2008/012607
§ 371 (c)(1),
(2), (4) Date: May 11, 2010

(87) PCT Pub. No.: WO2009/064373
PCT Pub. Date: May 22, 2009

(65) Prior Publication Data
US 2010/0266156 A1 Oct. 21, 2010

Related U.S. Application Data

(60) Provisional application No. 60/988,240, filed on Nov. 15, 2007.

(51) Int. Cl.
*G01J 4/00* (2006.01)
*G01N 21/00* (2006.01)

(52) U.S. Cl.
USPC .......................................... 356/364; 356/432

(58) Field of Classification Search
CPC ....... G01N 21/23; G01N 21/49; G01N 21/59; G01N 1/12; G01N 1/10; G01N 1/20; G01N 15/06; G01N 15/12; G01N 2015/047; G01N 2015/04
USPC ................ 356/244, 335–342, 364, 432, 445
See application file for complete search history.

(56) References Cited

U.S. PATENT DOCUMENTS 3,937,577 A * 2/1976 Dorsch .......................... 356/312
4,321,823 A * 3/1982 Anderson .................... 73/61.65
(Continued)

OTHER PUBLICATIONS

Bishop, "Towards an Autonomous Ocean Carbon Observatory," Interdisciplinary Colloquium, Lawerence Berkeley National Laboratory, Building 50 Auditorium, (Nov. 29, 2006).
(Continued)

*Primary Examiner* — Gregory J Toatley
*Assistant Examiner* — Rufus Phillips
(74) *Attorney, Agent, or Firm* — Lawrence Berkeley National Laboratory

(57) ABSTRACT

A robotic optical sedimentation recorder is described for the recordation of carbon flux in the oceans wherein both POC and PIC particles are captured at the open end of a submersible sampling platform, the captured particles allowed to drift down onto a collection plate where they can be imaged over time. The particles are imaged using three separate light sources, activated in sequence, one source being a back light, a second source being a side light to provide dark field illumination, and a third source comprising a cross polarized light source to illuminate birefringent particles. The recorder in one embodiment is attached to a buoyancy unit which is capable upon command for bringing the sedimentation recorder to a programmed depth below the ocean surface during recordation mode, and on command returning the unit to the ocean surface for transmission of recorded data and receipt of new instructions. The combined unit is provided with its own power source and is designed to operate autonomously in the ocean for extended periods of time.

20 Claims, 12 Drawing Sheets

(56) References Cited

U.S. PATENT DOCUMENTS

| | | | |
|---|---|---|---|
| 5,275,787 A * | 1/1994 | Yuguchi et al. | 422/82.08 |
| 6,313,943 B1 | 11/2001 | Ikado et al. | |
| 6,785,432 B2 * | 8/2004 | Letant et al. | 385/12 |
| 7,030,981 B2 * | 4/2006 | Bishop et al. | 356/368 |
| 2005/0126505 A1 * | 6/2005 | Gallager et al. | 119/234 |

OTHER PUBLICATIONS

International Search Report and Written Opinion for International Application No. PCT/US08/12607 mailed Jan. 27, 2009.

* cited by examiner

US 8,717,564 B2

OPTICAL SEDIMENTATION RECORDER

CROSS REFERENCE TO RELATED APPLICATIONS

This application claims the priority benefit to PCT Application PCT/US2008/012607, filed Nov. 7, 2008, entitled Optical Sedimentation Recorder, which in turn claimed the benefit of priority to U.S. Provisional Application 60/988,240 filed Nov. 15, 2007, the contents of both of said applications hereby incorporated herein by reference as if fully set forth in their entirety.

STATEMENT OF GOVERNMENTAL SUPPORT

The invention described and claimed herein was made in part utilizing funds supplied by the U.S. Department of Energy under Contract No. DE-AC03-76SF00098, and more recently under DE-AC02-05CH11231. The government has certain rights in this invention.

BACKGROUND OF THE INVENTION

1. Field of the Invention

This invention relates generally to a method of indirectly measuring the concentrations of carbon dioxide in the oceans, and more specifically to a robotic device which can operate autonomously in the oceans for extended periods of time, while recording carbon sediment flux at resolution times of minutes or hours over months to years.

2. Background of the Related Art

With the increasing concerns about climate change, and the role that the observed concentrations of carbon dioxide plays in this change, there is increasing interest in better understanding the carbon dioxide cycle with its interactions over land and sea. Because of the ease of accessibility, it is relatively easy to monitor the generation and discharge of $CO_2$ into the atmosphere. It is also reasonably possible to predict the capacity for land based plant matter using such processes as photosynthesis to convert atmospheric $CO_2$.

The atmospheric carbon inventory gains due to anthropogenic emissions are lower than expected because $CO_2$ is being taken up by land ecosystems and by the ocean. It has been estimated that about half of the carbon dioxide sink from the atmosphere is absorbed over land, and the other half absorbed over the oceans. This will change in the future.

Carbon dioxide once absorbed by the ocean waters, in its dissolved form is chemically converted into biomass by ocean going plant life such as plankton (under the influence of sunlight) which presently account for half of global photosynthesis. The absorption of extra $CO_2$ into the ocean causes acidification of surface waters and the impact on ocean photosynthesis is poorly understood.

Typically such biomass as it decays, and/or is consumed by aquatic life forms is converted into particulate organic carbon debris (POC) or sediment. The amount of generated sediment or detritus is a complex function of existing biomass. Some species of phytoplankton (such as coccolithophorids) also convert dissolved inorganic carbon during photosynthesis (biologic processes) into particulate inorganic carbon (PIC), which can take the form of biogenic particles of calcium carbonate ($CaCO_3$). This PIC component occurs as both calcite and aragonite mineral polymorphs of $CaCO_3$ in marine environments, ranging in concentration form less than 0.01 micromoles/liter in deep ocean waters to over 30 micromoles per liter in open ocean surface waters during phytoplankton blooms. Some zooplankton (i.e., Pteropods, Foraminifera) also make shells composed of calcite and aragonite. Coral reefs are also formed of aragonite. Acidification of seawater due to human generated $CO_2$ is believed to negatively impact both calcifying phytoplankton and zooplankton.

Despite the important role that the oceans play in the global carbon cycle and of the regulation of levels of atmospheric $CO_2$, the biological and physical processes that sequester carbon remain poorly understood. This is due in large part because of the difficulties of making continuous observations in the vast waters of the world's oceans, including those areas of extreme weather, ice, winds and the like. Yet, the upper kilometers of the ocean are both biologically quite active, and very observation-poor.

To date, most such $CO_2$ monitoring has been ship based, with sampling units placed at sea and ship tenders required to be in position to take periodic readings. Conventional ship based sampling methods such as the collecting of particles by filtration using rosette-mounted bottles or large volume in situ filtration cannot adequately capture the spatial and temporal variability of biomass material in the ocean. Further, such ship based tender is time consuming, and expensive, and this thus severely limits the number of sampling stations which can be established. Accordingly, there is a need for the development of an autonomous, robotic platform for real time monitoring of the biotic carbon flux on a continuous basis, a monitor which may be placed in an ocean environment and data collected for days, months and even years at a time without special tending, where data can be relayed in real time via satellite.

BRIEF SUMMARY OF THE INVENTION

By way of this invention an autonomous sampling platform has been developed which is capable of being placed at ocean depths for periods of time, collecting biomass debris, taking optical readings at controlled intervals of the amount of debris collected, and periodically surfacing to transmit the collected data from a stored accumulation of readings. In addition, the platform of this invention is self cleaning, and can be programmed to clean the collection stage of the device after a preset number of reading cycles.

In one embodiment the sampling platform of this invention can be coupled to a buoyancy engine which connects to the sampling apparatus, and contains its own communications system for satellite based transmission of collected data. We refer to this configuration which combines sampling platform and buoyancy engine as the Carbon Flux Explorer. The buoyancy engine is capable of deploying the sampling unit from the surface down to depths of 800 to 2,000 meters or more. It can be initially programmed to surface at preset time intervals for reporting of data to overhead satellites. It can also be remotely programmed when at the ocean's surface to adjust the diving/collection/surfacing interval to whatever time cycle is appropriate to the experiment or data collection function being overseen by the system's operator. The buoyancy engine can also be programmed to operate at a first depth for a period of time, and then to change depth for one or more subsequent sampling cycles.

The sampling platform includes a collector for capturing biomass particles as they sink, a transparent stage upon which the collected particles settle, and an imaging system for imaging the collected particles over set sampling increments. The imaging system itself operates in three modes for detection and recording of both POC and PIC debris. In one mode, an illumination source is positioned around the stage and used to sidelight collected particles (dark field). In a second mode a light source is positioned above the sample to provide backlit illumination of the collected particles (transmitted illumination). Finally, cross polarized transmitted light is used for illumination of birefringent PIC materials.

As used herein, birefringence refers to the ability of a mineral crystal to split an incident beam of linearly polarized light into two beams of unequal velocities (corresponding to two different refractive indices of the crystal) which subsequently recombine to form a beam of light that is no longer linearly polarized. The extreme birefringence of $CaCO_3$ (such as might be found in the shells of sea animals or calcareous phytoplankton) makes it appear to light up when viewed through cross polarizers. The extreme birefringence of calcium carbonate ($CaCO_3$) relative to other major components of marine particulate matter provides a basis for making optical in situ measurements of particulate inorganic carbon (PIC) in seawater. Because $CaCO_3$ particles dominate the mineral fraction of marine particulate matter and are much more birefringent than other major types of inorganic mineral particles, PIC is expected to be the dominant source of any birefringence signal.

The lighted stage images are recorded by a sensor such as a camera mounted below the stage and directed upwardly towards the stage and at right angles to the plane of the stage. In one embodiment, the camera can be a digital camera, and the coverage area of illuminated particles is recorded by counting the number of illuminated pixels. Optical resolutions of 15 micro meters have been achieved over an area of approximately 9 $cm^2$. In another embodiment a CCD camera can be used. In one embodiment, three sets of images of collected debris (back lit, side lit and back lit/cross polarized, taken in rapid succession one after the other) are obtained as part of each sampling event, which sampling event is programmed to take place at regular intervals. For example, sample imaging can be done in increments of every 20 minutes, 30 minutes, or in increments of hours, the interval a matter of choice of the platform operator.

The sampling platform (hereinafter interchangeably referred to as the sampling apparatus, sampling module, sampling station or optical sedimentation recorder) is designed to be self cleaning. Over time, as particles continue to accumulate, eventually the collection stage becomes completely covered with debris and thus opaque, preventing further collection of useful data. Accordingly, the unit is equipped with a pumping system that withdraws ocean water though a ring surrounding the stage at its periphery, the ring including fluid channels so disposed as to cause fluid within the imaging area to swirl as it is withdrawn from the imaging chamber. This induced circular flow effectuates a hydrodynamic cleaning of the sedimentation stage. The cleaning function can be performed once every predetermined numbers of samplings. In another embodiment, where sampling intervals are programmed to occur every 30 minutes, cleaning can be performed once every 3-6 hours. Immediately after a cleaning event, a further sampling is taken to document the "clean state" of the stage for the next set of sampling cycles.

The sampling station includes a recorder such as a computer which collects and stores information from the imaging camera, as well as contains the programs that control the operation of the optical sediment station. In the carbon flux explorer (CFE) configuration, this computing system is electronically linked to the bouyancy module or engine which has the capability for sending and receiving information to and from an overhead communication link such as a satellite. Data are also retained onboard in non-volatile memory.

The sampling module can be deployed in several modes. In one mode it can be affixed to a cable moored to a buoy and simply allowed to sink to a fixed depth, the depth limited by the length of the attached cable. In the carbon flux recorder mode, the sampling module is attached to a buoyancy vehicle, such as one produced by the Instrument Development Group of the Scripps Institution of Oceanography, and set adrift, to be positioned at various depths. In yet another embodiment, in either mode, multiple sampling modules can be deployed together. Using such a multiple deployment affords several advantages, one of them being that readings of the multiple units can be compared, as a means of calibrating one against the other. In addition, due to the long duty cycle of these sedimentation recorders, and the expense of positioning them, the one unit can serve as a backup to the other unit in case of battery, or other type of component failure.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION

The various features and advantages of the present invention will become more fully apparent from the following description taken in conjunction with aforementioned drawings.

Figure 1A:
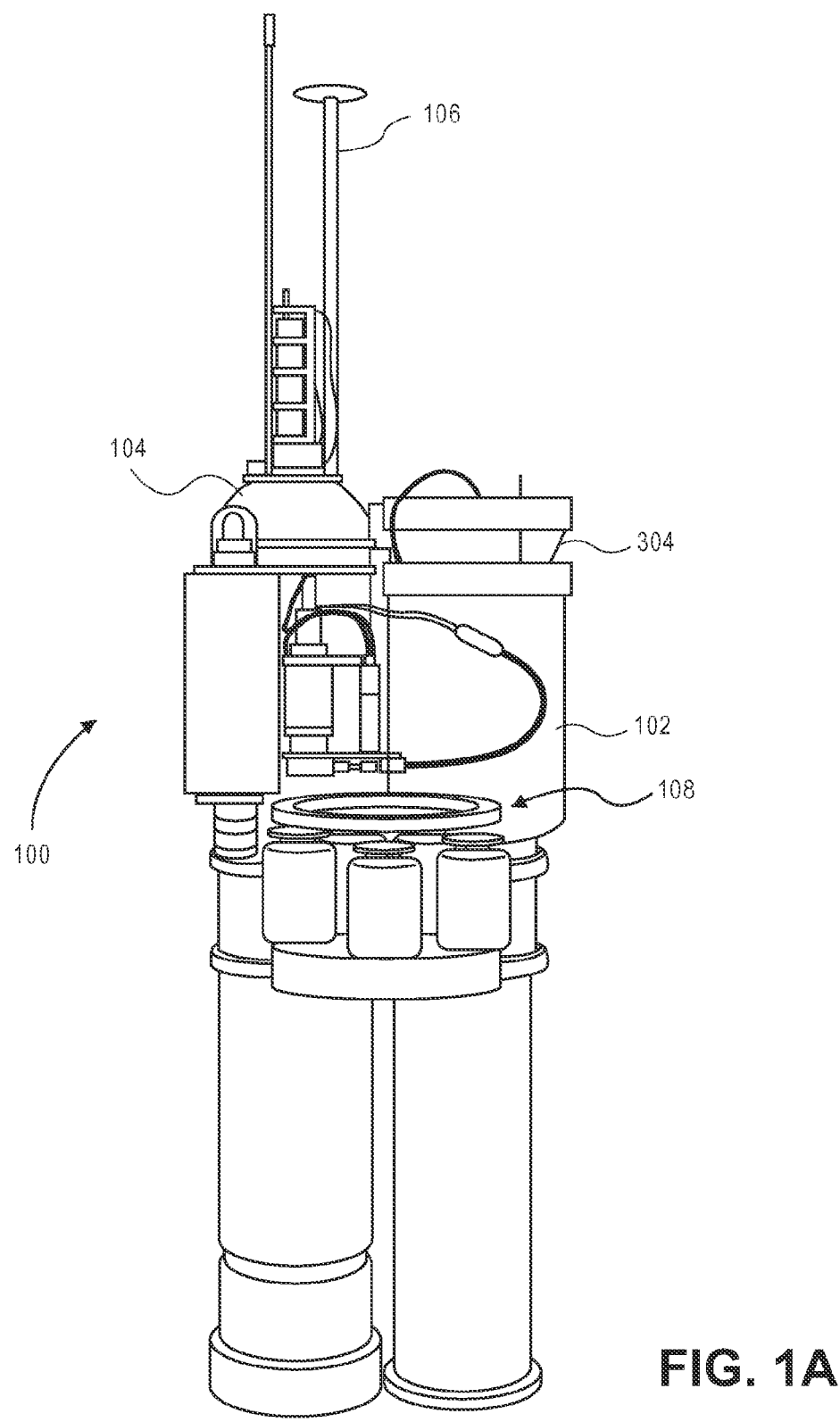
FIG. 1A is an illustration of an arrangement of the optical sedimentation recorder affixed to a buoyancy engine according to an embodiment of this invention.

With reference now to FIG. 1A, the carbon flux explorer unit of the invention 100 is illustrated, with sampling platform 102 joined to buoyancy engine 104, a profiling float. Batteries (not shown) in both units are used to power the various mechanical devices (such as pumps, etc) illuminator lamps, and electronic components. A transmission cable (also not shown) allows for cross communication of data and computer commands between platform 102 and buoyancy engine 104. A satellite communications unit incorporated into module 104 is designed to uplink to overhead satellites through satellite antenna 106 when the carbon flux explorer is at the ocean's surface.

Unit 100 is designed to free float once placed in the ocean, and follows the currents in a lagrangian fashion. Because of this relatively random motion a locator function is provided by an on board GPS unit in combination with the satellite link previously described. The locator function of the CFE is primary in providing real time position (i.e. longitude and latitude) information which can be coordinated with each sampling, for proper data analysis and interpretation. In addition, should it be necessary to recover the CFE for repair, replacement, securing of collected samples and the like, the GPS unit can be used to facilitate recovery.

Figure 1B:
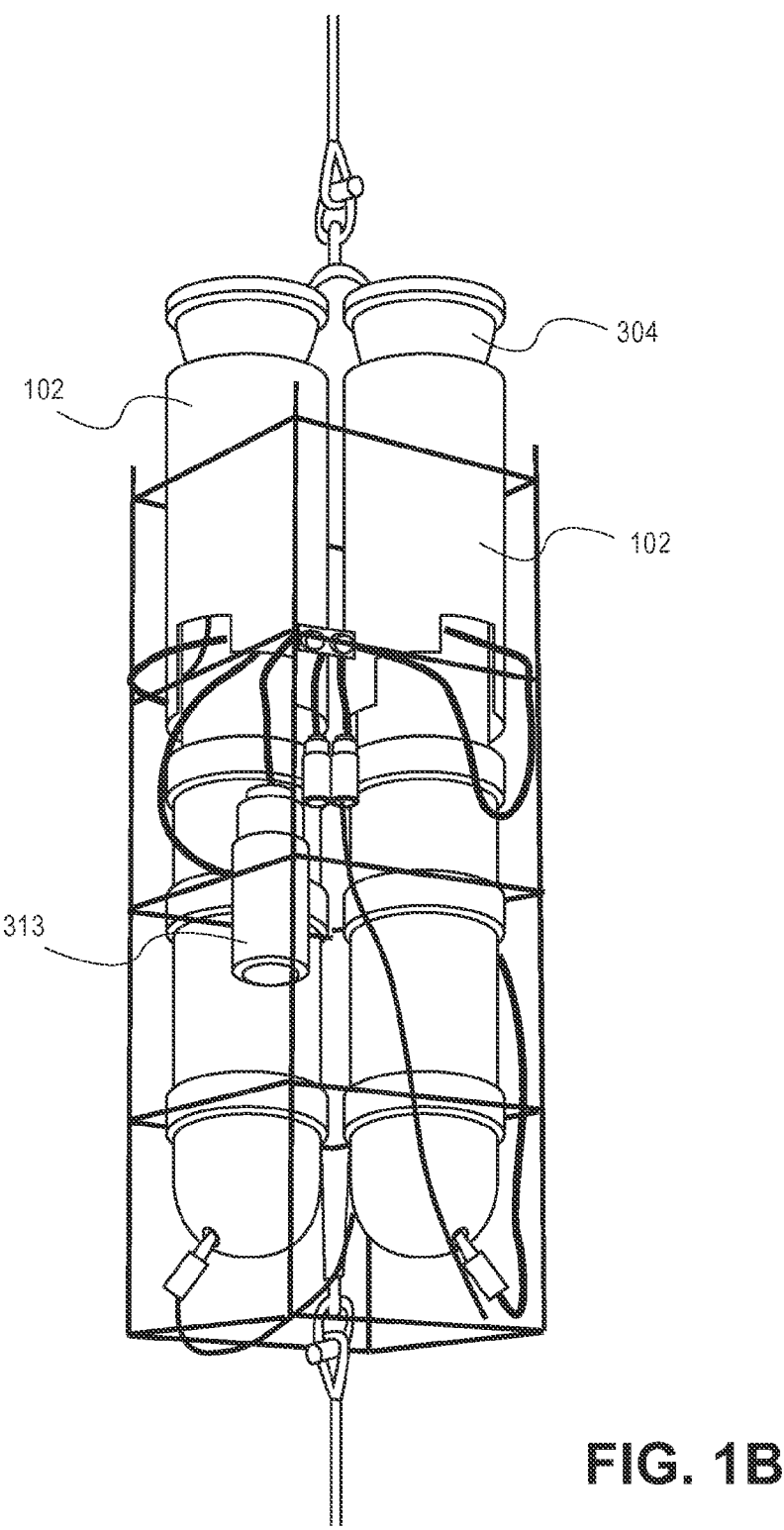
FIG. 1B is an illustration of a paired arrangement of optical sedimentation recorders in cable suspension mode according to an embodiment of this invention.
Figure 2:
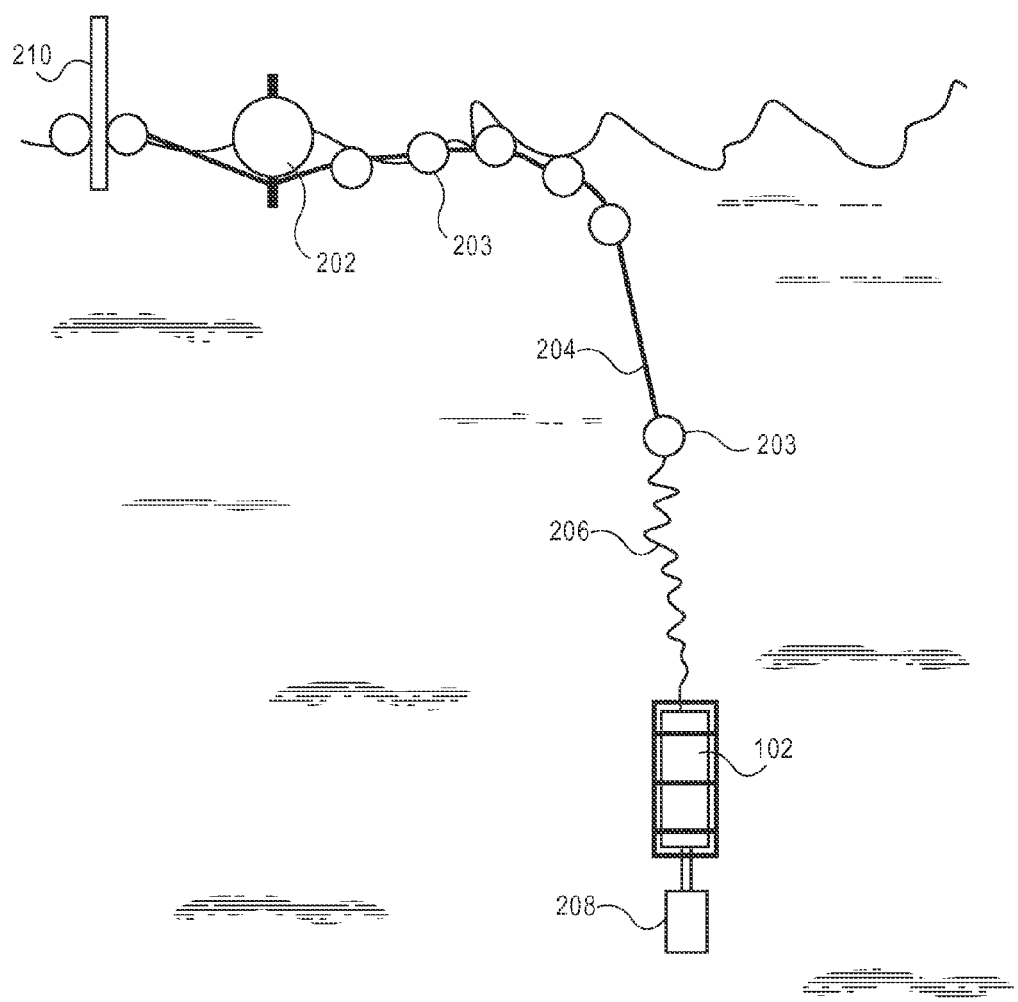
FIG. 2 is a side view of the paired optical sedimentation recorders of FIG. 1B tethered below a free drifting buoy system.
Figure 3:
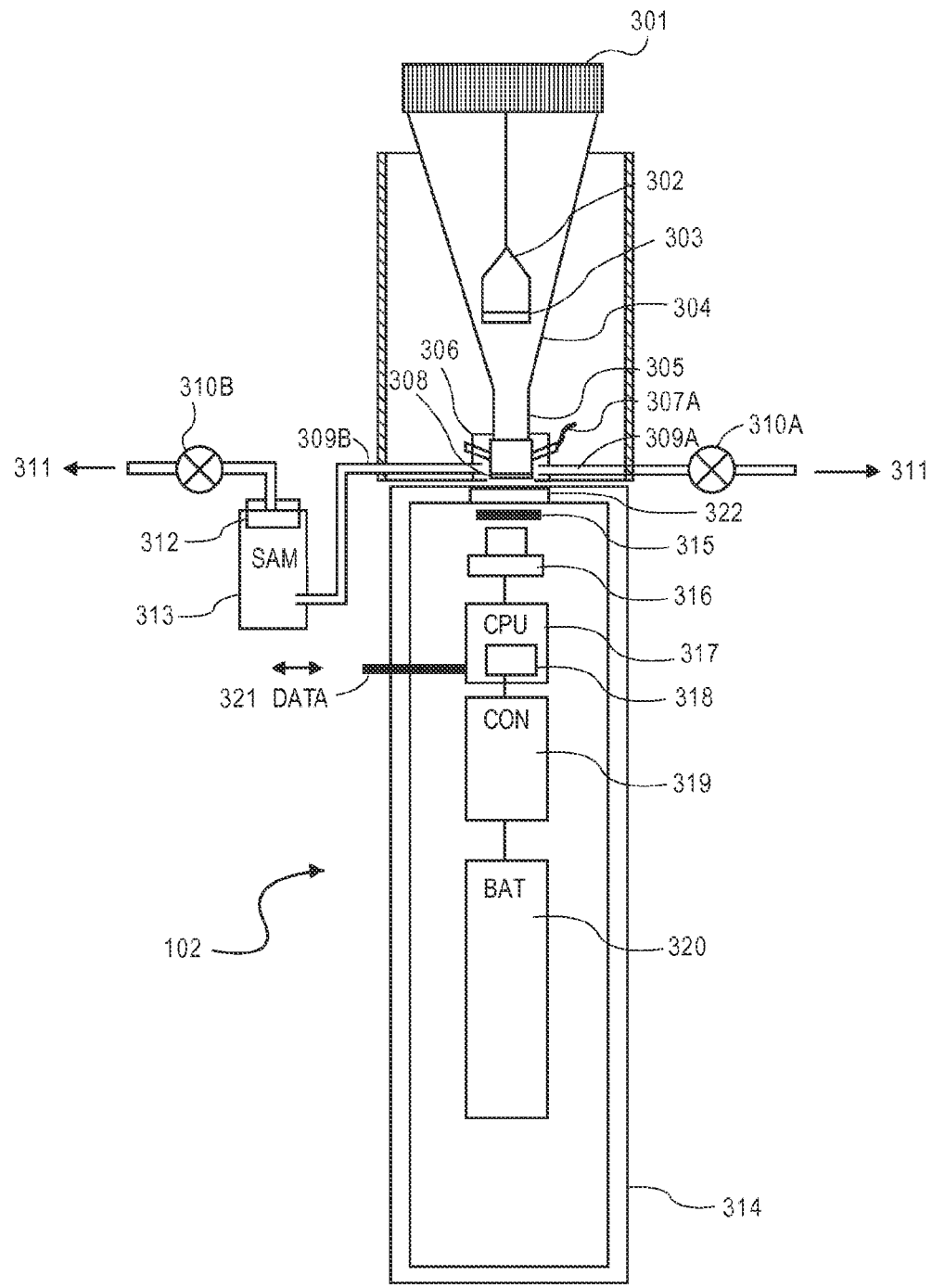
FIG. 3 is a cut away schematic of an optical sedimentation recorder.
Figure 4A:
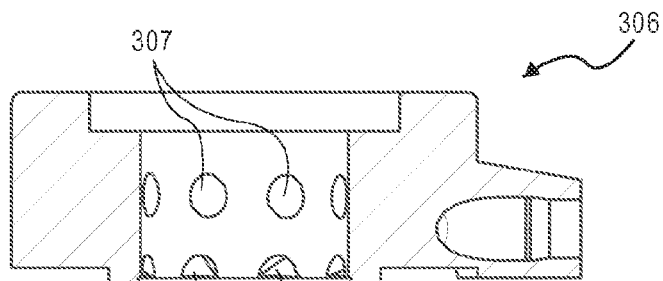
FIGS. 4A-4E are top, side and isometric, views of the combined illuminator/cleaner/collector ring according to an embodiment of this invention.
Figure 4B:
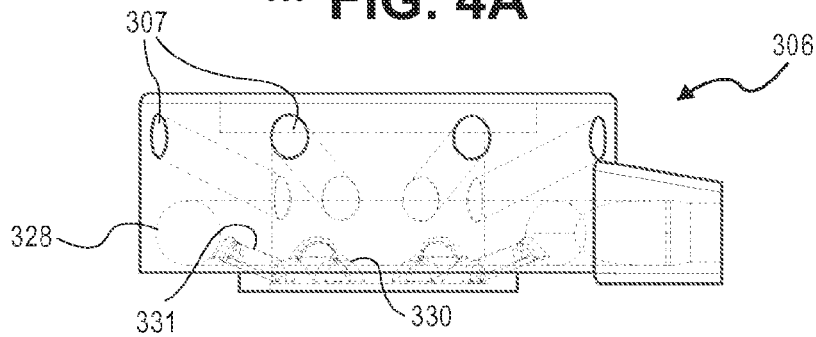
Figure 4C:
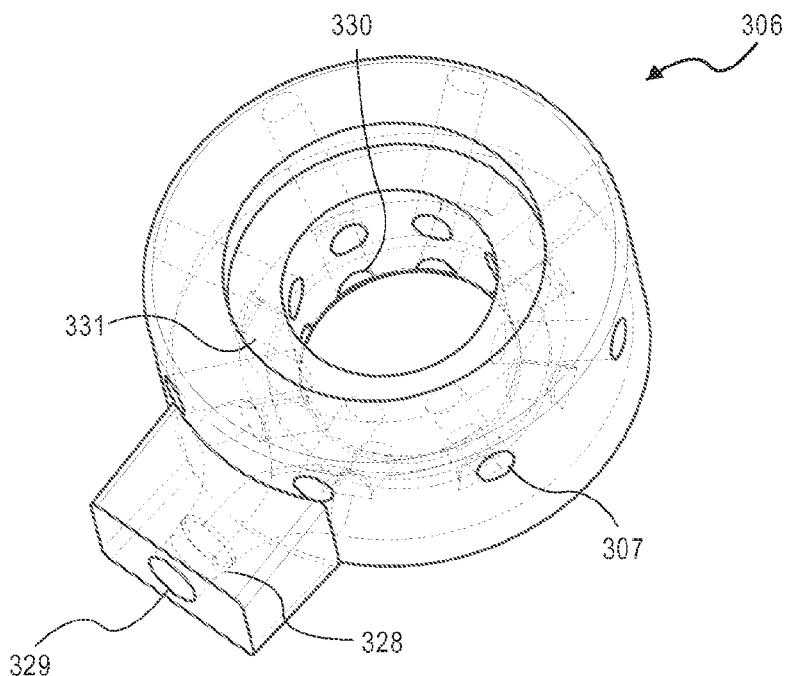
Figure 4D:
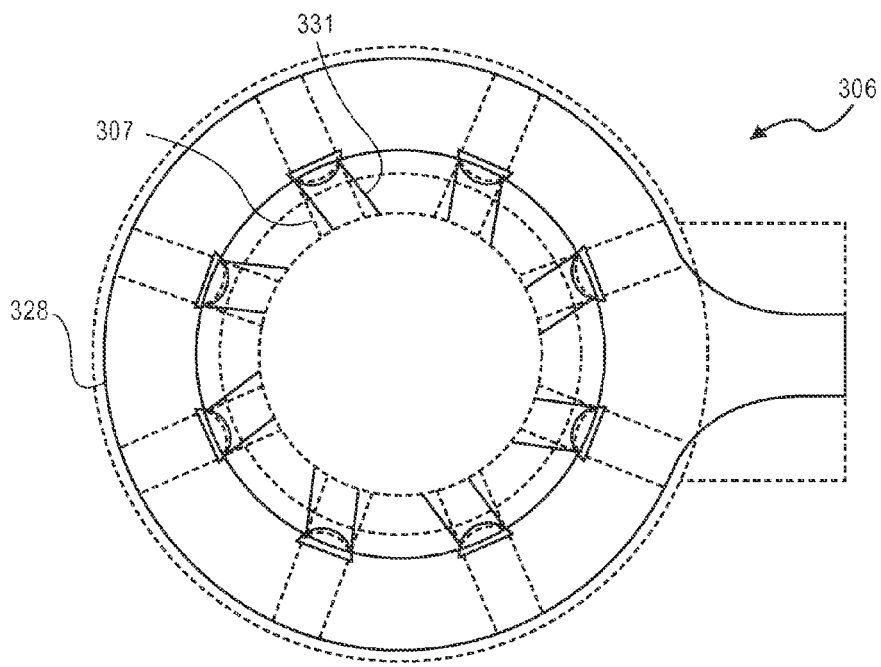
Figure 4E:
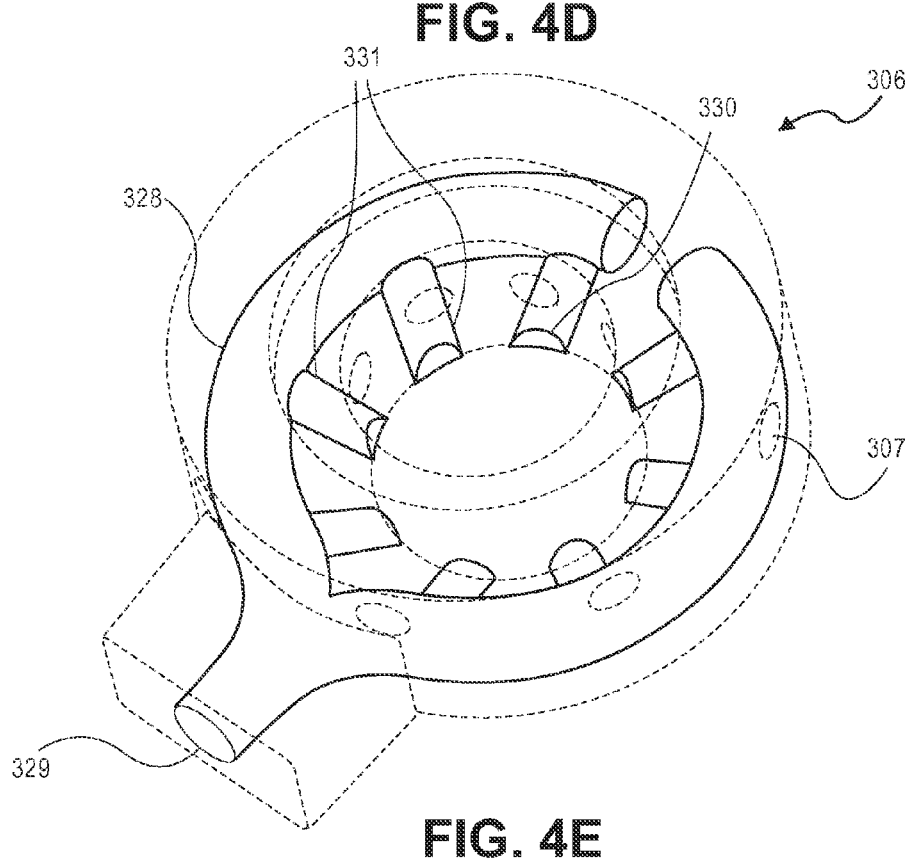

With reference now to FIGS. 1B and 2, an alternative arrangement is shown where two sampling platforms are combined, side by side, to operate independently one from the other. In this mode, the optical sediment recorders 102 are mounted to a cable, and suspended at depth by main buoy 202, and flotation members 203. Cable 204, which may be a nylon rope, connects carbon flux recorders 102 to the flotation system. The rope may be terminated using an elastomer damping system 206, designed to further damp the tugging effects as surface waves move the main buoy 202 up and down. A logging CTD-Depth recorder 208 is used to document the depth to which the recorder has descended at the time readings are taken. The unit logs temperature, salinity, and pressure, and may include other biomass sensors, all logged information stored until recovery. GPS and ARGOS tracking unit 210 is provided as a navigation device to aid in locating the unit for retrieval. In one alternative embodiment, 3 or more units can be strapped together to provide a sampling station combining a number of sampling platforms. In this way multiple experiments can be performed simultaneously. In another embodiment, the recorder could be deployed off shore, on a deep sea ocean mooring, which can be either surface-tethered or fixed to the ocean bottom. In such circumstance, collected data may be communicated via the mooring cable to shore. In yet a still further embodiment, the autonomous unit of FIG. 1 can be combined into clusters of two or more units, or a single buoyancy engine combined with two or more sampling platforms for conducting simultaneous experiments With reference now to FIGS. 3, and 4, in FIG. 3 a cut-away side elevation of the sampling platform (optical sedimentation recorder) of this invention is depicted. Falling biomass particles (whether POC or PIC, or non carbon containing material such as silica) are captured by collector 304 as they drift downwardly in the ocean. While collector 304 as illustrated is depicted as a funnel, the use of a funnel is not required. The collector can instead by a simple cylinder. However, the funnel serves to concentrate the particles in the sample collection area, and thus facilitates the use of a smaller sample collection plate 308. Settling chamber 305 directs the captured particles to collection plate 308. In another embodiment, settling chamber 305 can be eliminated and collector 304 terminated at the sample chamber defined by light support ring or collar 306. Preferably, the inside surface of collector 304 is polished so that captured particles easily slide down its walls to collector plate 308. Plate 308, a planar transparent stage having a front and back side, and can be made of glass. In one embodiment, the plate can have inscribed thereupon ruler or scale marks for focus and size reference.

Settling chamber 305 (collector 304, when there is no settling chamber) terminates at a sample chamber defined by light support ring or collar 306, a donut shaped structure incorporating ports 307 (see FIG. 4) which house LED lights 307A. In turn, collar 306 terminates at collector plate 308, to which it is fixedly attached. Collar 306 can be made from any chemically stable, easily formed material, and in one embodiment is made of plastic. Collar 306 may also be slightly tapered to a larger radius in the upward direction, away from sample plate 308. In this way it is less likely that the camera/sensor will image the walls of collar 306. Fluid ports 330 of collar 306 are used in connection with a hydrodynamic cleaning system, later discussed.

The optical lighting system comprises a number of separate components. Down-light source 302 is rigidly affixed to collector 304 and positioned in symmetrical alignment with the sample area of collection plate 308. Light source 302 should be stable in its illumination intensity, provide even illumination, and be of sufficient brightness for acquisition of properly exposed cross-polarized images. In one embodiment, back lit source 302 consists of an array of regulated LEDs cast in transparent plastic, followed by a diffuser to even out the illumination, and a fixed linear polarizer. Separate LED side light sources 307A used for dark field illumination of particles comprise one or more sources directionally positioned to shine their light across collection plate 308. Both down light 302 and side lights 307A may be rheostatically controlled such that the intensity of the lights may be independently regulated. Alternatively, the intensity of the lights may be set at the pre-deployment stage, and image adjustments made by changing imaging parameters of the camera, such as exposure time, aperture setting, etc.

Baffle 301 is positioned above collector 304 to filter out stray sunlight in the vicinity of the collector opening, while being porous so as to permit particles to enter into the collecting chamber. In one embodiment, baffle 301 is formed from honeycomb material which serves to collimate ambient light, and thus help reduce ambient background. In another embodiment the baffle comprises aluminum which is painted black to further eliminate unwanted background light.

The third light source (for the detection of birefringent materials) is cross polarized. The first element of the source is polarizer plate 303 which is placed in front of down-light source 302. In one embodiment, the polarizer element is fixedly mounted in front of the down-light assembly. The second polarizer element 315 is rotatably mounted below collection plate 308, and in front of imaging system 316. Element 315 is rotated in a plane parallel to the plane of fixed polarizer plate 303 and can be rotated from 0 to 90 degrees, relative to the polarization orientation of fixed plate 303. When the transmission axes are perpendicular to each other, transmission of incident light from source 302 is minimized. Thus, what is actually measured is light passing through first polarizer 303 that has had its linear polarization removed by interaction with birefringent particles deposited on collection plate 308. Light having interacted with the birefringent particles is no longer linearly polarized and therefore passes through the second polarizer. The amount of light reaching the imaging system is proportional to the amount of birefringent material present on the collection plate. See related U.S. Pat. No. 7,030,981 for a further discussion of the use of cross polarization as a technique for birefringent particle detection.

Imaging system 316 may be a custom imaging sensor or a commercial digital camera system. In one embodiment, the sensor or camera can be non-focusing, in the case where brightness of particles in the sample area is to be measured. Such a simple, unfocused sensor system records aggregated brightness alone, permitting recordation of the rate of debris accumulation. In another embodiment, using a focusable sensor or camera, defined images are obtained, providing additional information regarding particle class, size, shape, and other properties, as well as allowing for particle size distribution determination. In experimental work to date, a focusable Nikon Coolpix 5700 camera was used for imaging. Such a focusable camera allows for readings to be taken both at various focal distances, shutter speeds, and aperture settings.

The camera is powered and controlled using a microcontroller and single board computer. Custom firmware and software of these systems set camera parameters, lighting, sampling interval, and cleaning functions. They further trigger the camera to take photographs and the data are downloaded from the camera for storage on non-volatile compact flash memory and later processing using the computer.

The digital images collected by imaging system 316 are stored in computer 317, the computer in communication with the imager, and programmed to analyze and store data in memory 318. The computer (which can be single board) can be preprogrammed to run the various devices of the sampling platform, to control and monitor the various sampling cycles, turn lights on and off, instruct buoyancy member 104, and regulate the sending of data to the communications system. Controller 319 (which can be a single board controller) supports essential functions of the platform during sleep and awake modes, and controls power distribution to all of the internal and in one embodiment all of the external powered systems. The controller also measures instrument attitude (or tilt) at periodic intervals as well as other parameters such as instrument temperature and battery voltages. In one embodiment, controller 319 may additionally be used to control the imager and manage the storage of data. Battery 320 supplies the DC power needs for the system. Cable 321 is a bi-directional data cable for transport of data to the communications module for sending data, and receiving incoming commands. The optical imaging components and supporting computer, controller and battery power modules are contained within a water tight pressure case 314 which includes an optical window 322 disposed below sample plate 308.

In remote sampling mode, the Carbon Flux Explorer can be preprogrammed to periodically image the collection stage and report results. For example, samplings can be made at any desired interval, such as every 15, 20, or 30 minutes, or longer over a 24 hour period, each sampling comprising the processing of three images (i.e. transmitted, cross-polarized, and dark field). The unit can alternatively be programmed to collect images during daylight hours only or conversely during nighttime hours only. In addition, the cleaning interval can be programmed as desired, such as once every 3-6 hours, or after a given number of samplings. For data transmission, the unit can be programmed to surface at regular intervals, such as once or twice a day, the duty cycle a matter of operator choice. In another embodiment where the optical sedimentation recorder is submerged suspended by cable, the unit can be brought to the surface at any time at the discretion of the unit's ship-in-residence operator. Also, a plurality of particle collection samples can be obtained, in one embodiment during cleaning mode, as described in the next paragraph, using a carousel type bottle collection unit 108 such as the one illustrated in FIG. 1A. In this embodiment, the sedimentation recorder is brought to the surface, the bottles of unit 108 recovered after all have been filled and debris analysis then conducted.

As collection plate 308 tends to be covered by collected debris in relatively short periods of time, it becomes vital to the continued operation of the station to provide for automated cleaning of the collection plate and chamber. With reference to FIG. 4 A-E, this is accomplished with hydrodynamic cleaning (i.e. flushing) where water is pumped over the plate to virtually blow particles away. In this embodiment, a small pump 311 (not otherwise shown) is placed at the end of sample evacuation line 309A (see FIG. 3) which includes isolation valve 310A, the valve normally in the closed position during sampling, and opened during cleaning. With the pump turned on, water is drawn in through open collector 304 down into the collection chamber, and through multiple mouse-hole openings 330 at the base of collar 306, and into channel(s) 331 to be exhausted to the ocean waters. Channel(s) 331 are ramped upwardly in a direction away from the chamber wall to prevent unintended particle loss from the imaging area. They are also sufficiently angled relative to the inner wall of collar 306 so as to impart a swirling motion to water within the sampling chamber as water is withdrawn from the chamber. Typically (though not critical), the channels extending from mouse hole openings 330 are ramped at approximately 20 degrees upwardly from the floor of the collection chamber, and are angled at about 10° to about 30° from a line normal to the collection chamber's inner wall.

An exhaust manifold 328 is provided interior of collar 306 which is in fluid communication both with channels 331, and fluid evacuation line 309A. In sample recovery mode, particulate samples can be collected during cleaning whereby, with isolation valve 310B in the open position, evacuated fluid is directed via line 309B to sample bottle 313, before being discharged to the open ocean. Line 309B connects to bottle 13 along its side, but above its bottom, to prevent loss of collected sample once the bottle is detached from unit 102. Particles swept from plate 308 are collected in sample bottle 313 and retained by a mesh or outlet filter 312. The collection of such sample material may be useful for later calibration in terms of carbon flux of the image data. In other words, samples representing specific image sets may be analyzed for POC, PIC and Si—thus facilitating the conversion of image data to chemical flux measurements. In another embodiment, for more detailed calibrations, several sample bottles may be provided and multiple samples collected over time.

Figure 5:
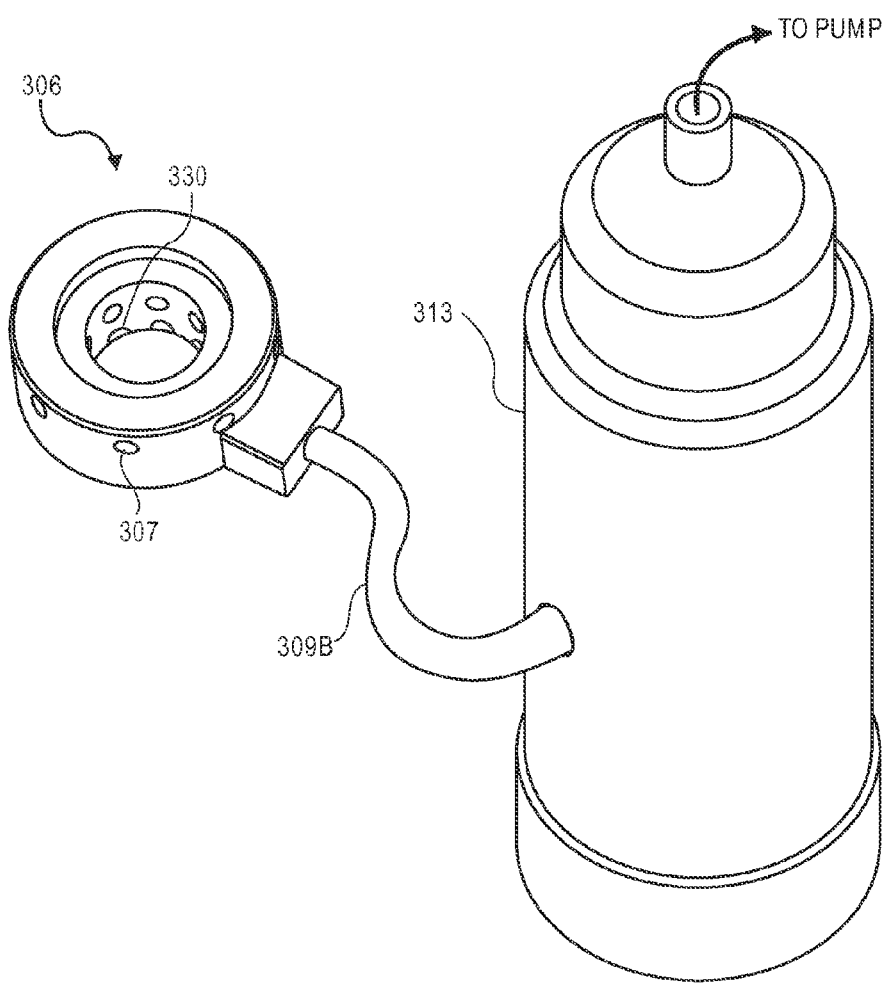
FIG. 5 is illustrative of one arrangement of the illuminator/cleaner/collector ring of FIG. 4 connected to a sampling bottle.

In one embodiment, as shown in FIG. 5, Manifold 328 is provided with a single exhaust outlet 329, connected to evacuation line 309B. In this embodiment the sample recovery option is provided as an alternative to direction discharge to the ocean through evacuation line 309A. In another embodiment, both lines 309A and 309B can be provided, the exhaust system outlet modified such that outflow from manifold 328 can be directed to either of the two evacuation lines, or outlet line 309 can be split into two separate branches, 309A and 309B.

Figure 6:
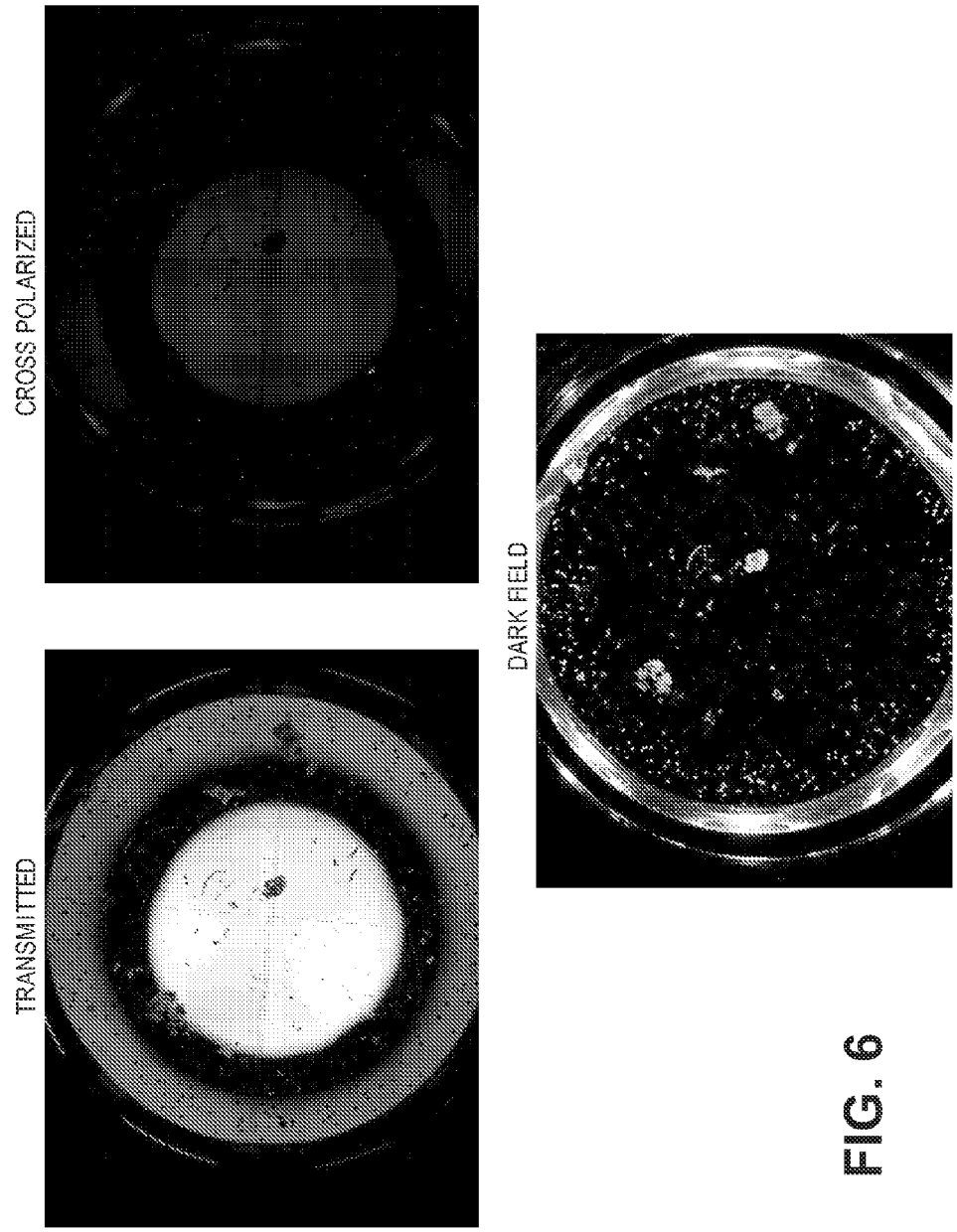
FIG. 6 depicts the original images for a single sampling comprising transmitted (back lit), dark field (side lit), and cross polarized back-lit images.
Figure 7:
FIGS. 7 and 8 are processed dark field (side lit) images for a separate sequence of samplings taken 40 minutes apart to illustrate the accumulation of particles over time.
Figure 8:
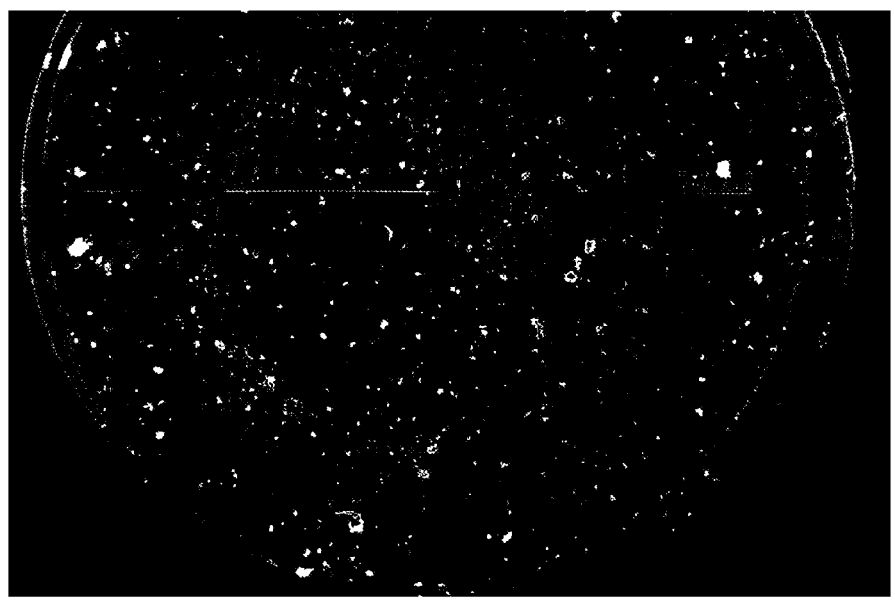
Figure 9:
FIG. 9 is a processed dark field image of the same sampling platform post sequence samplings of FIGS. 7 and 8, and after hydrodynamic cleaning.
Figure 10:
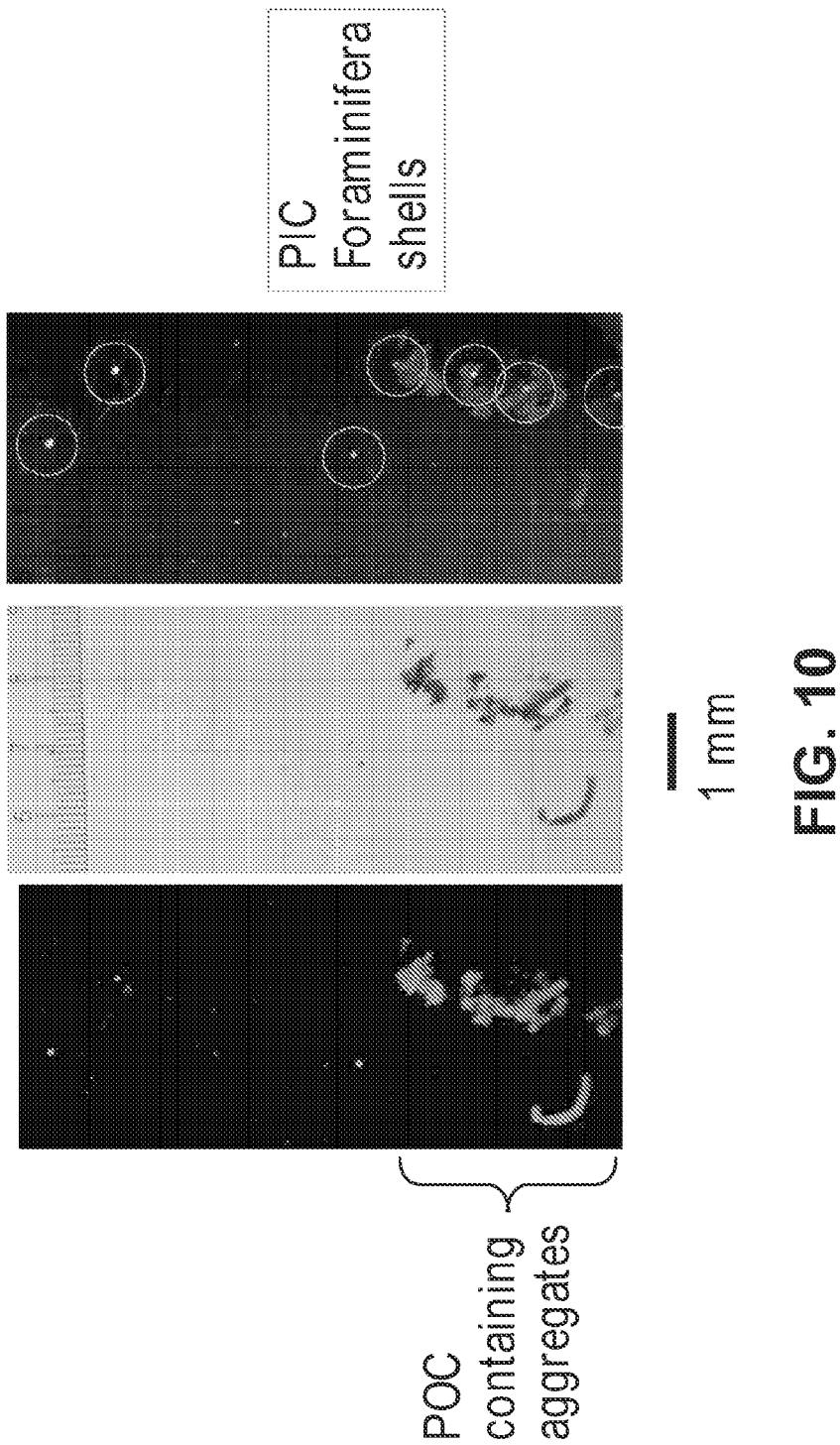
FIG. 10 depicts processed transmitted and cross polarized images of collected sedimentation including calcium carbonate foraminifera highlighted by cross polarized illumination.

Processed sampling images taken during various experiments are presented in FIGS. 6, 7, 8, 9 and 10. With reference to FIG. 6, a single sampling is depicted, the images taken one after the other, wherein collection plate 308 is sequentially first illuminated by light source 301 in transmitted (i.e. back lit) mode (top left), then polarizer 315 rotated 90 degrees from polarizer 303 in cross-polarized mode for illumination of birefringent material (top right—in this sampling there being no birefringent debris), and LEDs 307A activated in dark field mode (bottom). FIGS. 7, 8 and 9 depict dark field illumination images obtained during the same sampling cycle, FIG. 7 a photograph taken at 2:00 hours into the collection cycle, and FIG. 8 taken at 2:40 hours into the same cycle. FIG. 9 depicts the condition of collection plate 308 at 3:20 hours into the cycle, just after hydrodynamic cleaning of the plate. Lastly, the images of FIG. 10 illustrate the highlighting of birefringent material in cross polarized mode.

This invention has been described herein in considerable detail to provide those skilled in the art with information relevant to apply the novel principles and to construct and use such specialized components as are required. Although the invention has been described with respect to exemplary embodiments thereof, it should be understood by those skilled in the art that the foregoing and various other changes, omissions and additions in the form and detail thereof may be made therein without departing from the spirit and scope of the invention. By way of one example, though the carbon flux explorer has been described in the context of a combined sampling platform and buoyancy/communications engine, both the buoyancy functions could be incorporated into the sampling module itself, and the other functions of the buoyancy and communications module such as satellite telemetry, location functionality, etc. could be similarly incorporated. By way of a second example, first polarizer element 303 of the sedimentation recorder can be mounted so that it, rather than polarizer element 315, is rotatable. Important is that at least one or both of the polarizer elements can be rotated relative of one to the other, in a fashion such that the combined rotation approaches or exceeds 90 degrees. It is to be further understood that the invention can be carried out using different equipment, materials and devices, and that various modifications, both as to the equipment and operating procedures, can be accomplished without departing from the scope of the invention itself.

I claim:

1. An apparatus including:
a collector configured to capture particles;
a sampling chamber in fluid communication with the collector configured to receive and to confine the particles;
a transparent collection plate mounted to the bottom of the sampling chamber and positioned to have the particles deposited thereon;
a system configured to illuminate the particles deposited on the collection plate, the system including a bright field illumination source, a dark field illumination source, and a cross polarized illumination source, the bright field illumination source being rigidly affixed to the collector and being positioned in symmetrical alignment with the transparent collection plate;
an imaging system configured to capture images of the particles deposited on the transparent collection plate; and
a recording device configured to record the images.

2. The apparatus of claim 1 wherein the imaging system includes a digital camera.

3. The apparatus of claim 1 wherein the collector includes a funnel.

4. The apparatus of claim 1 wherein the recording device includes a controller or a computer.

5. The apparatus of claim 1 further including:
a cleaning module configured to remove the particles deposited on the transparent collection plate from the transparent collection plate.

6. The apparatus of claim 5 wherein the cleaning module includes a pump, transport lines, and openings disposed through a wall of the sampling chamber, wherein the openings are configured to provide for tangential like flow of incoming water around an inside wall of the sampling chamber, and wherein the cleaning module is configured to generate a body of swirling water overtop the transparent collection plate.

7. The apparatus of claim 1 further including:
a buoyancy unit configured to take the apparatus to depths below a surface of a body of water and to return the apparatus to the surface.

8. The apparatus of claim 1 further including:
a first device configured to process and to reduce the images; and
a second device configured to relay the images to shore or ship based stations.

9. A method employing the apparatus of claim 1, the method comprising:
collecting the particles over a period of time;
sampling the particles by capturing images of the particles deposited on the transparent collection plate, the sampling comprising capturing back light, side light, and cross polarized images;
recording the images; and
transmitting the images to one or more remote receiving units.

10. The apparatus of claim 1 wherein the transparent collection plate is positioned substantially perpendicular to a flow direction of the particles.

11. A method comprising:
providing an apparatus, the apparatus comprising:
a collector configured to capture particles,
a sampling chamber in fluid communication with the collector configured to receive and to confine the particles,
a collection plate mounted to the bottom of the sampling chamber and positioned to have the particles deposited thereon,
a system configured to illuminate the particles deposited on the collection plate, the system including a bright field illumination source, a dark field illumination source, and a cross polarized illumination source, the bright field illumination source being rigidly affixed to the collector and being positioned in symmetrical alignment with the collection plate,
an imaging system configured to capture images of the particles deposited on the collection plate, and
a recording device configured to record the images;
submersing the apparatus to a depth below a surface of water;
collecting particles over a period of time, the particles being deposited on the collection plate;
acquiring images of the particles, wherein the acquiring operation includes imaging the particles deposited on the collection plate using transmitted light, cross polarized light, and side light; and
storing the images.

12. The method of claim 11 wherein the storing operation includes storing the images on a computer.

13. The method of claim 11 wherein the acquiring operation is repeated.

14. The method of claim 13 wherein the acquiring operation is conducted on a periodic basis.

15. The method of claim 11 wherein the collection plate is a transparent collection plate.

16. The method of claim 11 further comprising flushing the particles deposited on the collection plate from a surface of the collection plate.

17. The method of claim 16 wherein the flushing operation is performed by hydrodynamic cleaning wherein water is drawn over the collection plate in a swirling motion.

18. The method of claim 13 further comprising transporting the apparatus to the surface of the water after performing a plurality of acquiring operations.

19. The method of claim 18 further comprising transmitting the images to one or more remote receiving stations.

20. The method of claim 11 wherein the collection plate is positioned substantially perpendicular to a flow direction of the particles.

\* \* \* \* \*